United States Patent
Le Bourhis

[11] Patent Number: 6,113,923
[45] Date of Patent: *Sep. 5, 2000

[54] AEROSOL COSMETIC COMPOSITIONS, AEROSOLS CONTAINING THEM AND USES

[75] Inventor: François Le Bourhis, Aubervilliers, France

[73] Assignee: L'Oreal, Paris, France

[*] Notice: This patent issued on a continued prosecution application filed under 37 CFR 1.53(d), and is subject to the twenty year patent term provisions of 35 U.S.C. 154(a)(2).

[21] Appl. No.: 08/372,395

[22] Filed: Jan. 13, 1995

[30] Foreign Application Priority Data

Jan. 14, 1994 [FR] France ................................ 94 00367

[51] Int. Cl.$^7$ ............................. A61K 6/00; A61K 9/04; A61K 7/06
[52] U.S. Cl. ........................ 424/401; 424/45; 424/70.1; 424/70.16
[58] Field of Search .................... 424/47, DIG. 1, 424/DIG. 2, 78.02, 70.11, 401, 45, 70.1, 70.16; 514/957, 945

[56] References Cited

U.S. PATENT DOCUMENTS

| | | | |
|---|---|---|---|
| 4,767,613 | 8/1988 | Nuber et al. | 424/47 |
| 4,897,262 | 1/1990 | Nandagiri et al. | 424/70.11 |
| 5,021,238 | 6/1991 | Martino et al. | 424/47 |
| 5,158,762 | 10/1992 | Pierce | 424/47 |
| 5,164,177 | 11/1992 | Bhatt et al. | 424/47 |
| 5,362,486 | 11/1994 | Nandagiri et al. | 424/47 |
| 5,900,229 | 5/1999 | Dupuis | 424/47 |

FOREIGN PATENT DOCUMENTS

| | | |
|---|---|---|
| 0257444 | 3/1988 | European Pat. Off. . |
| 0455081 | 11/1991 | European Pat. Off. . |
| 0523388 | 1/1993 | European Pat. Off. . |
| 0557087 | 8/1993 | European Pat. Off. . |
| 0574607 | 12/1993 | European Pat. Off. . |
| 2098226 | 11/1982 | United Kingdom . |

OTHER PUBLICATIONS

Oteri, R. et al. (1991). Cosmetics & Toiletries, vol. 106, pp. 29–34.
Martino, G. T. et al. (1992). Spray Technology & Marketing, Mar. Issue, pp. 34–39.
Derwent Abstract of DE–A–4013872.

*Primary Examiner*—Thurman K. Page
*Assistant Examiner*—Blessing Fubara
*Attorney, Agent, or Firm*—Finnegan, Henderson, Farabow, Garrett and Dunner, LLP

[57] ABSTRACT

A cosmetic composition comprising a pressurized aerosol composition spontaneously forming a foam on contact with a surface to which it is applied, in particular keratinous material such as hair, the aerosol composition comprising: (i) an aqueous liquid vehicle containing at least one foaming anionic polymer and/or at least one foaming cationic polymer; and (ii) a mixture of propellants containing dimethyl ether and at least one other propellant selected from volatile alkanes, volatile haloalkanes and mixtures thereof. The composition is used in particular as a hair setting, blow drying, hair shaping or styling composition.

47 Claims, 1 Drawing Sheet

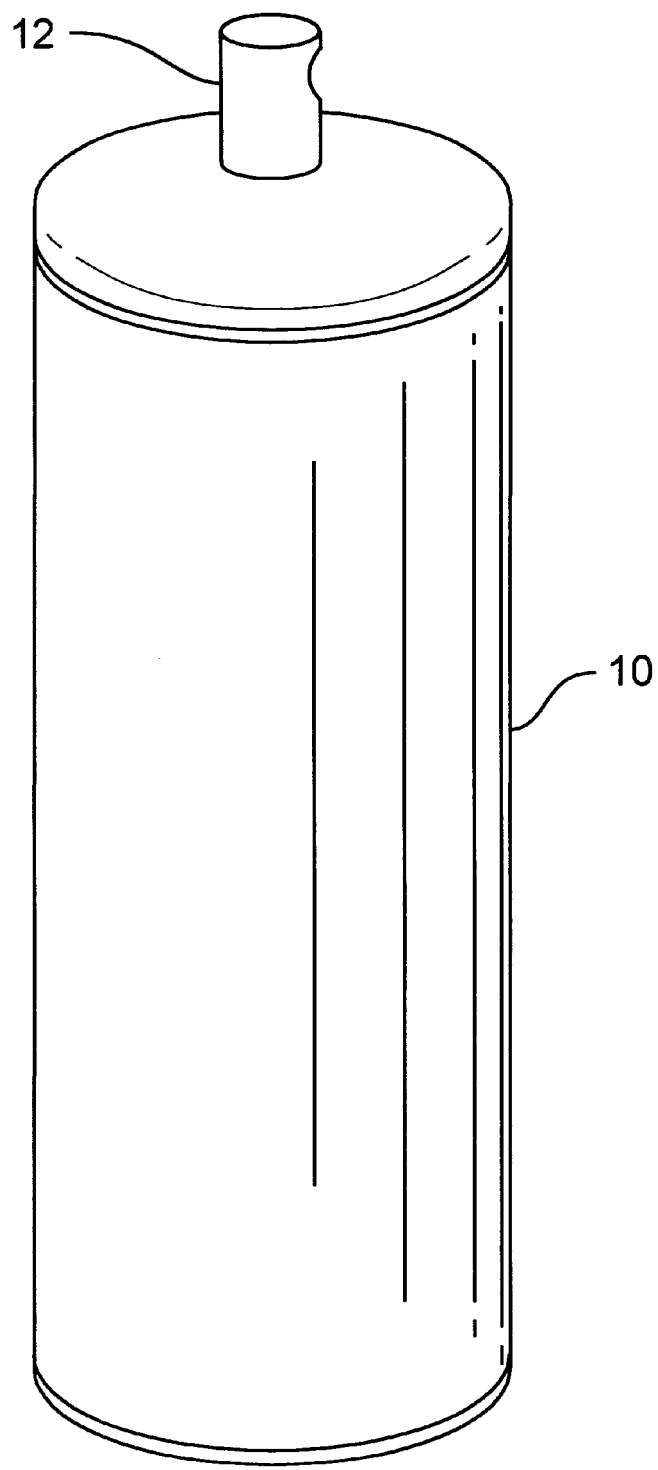
FIGURE

AEROSOL COSMETIC COMPOSITIONS, AEROSOLS CONTAINING THEM AND USES

The present invention is directed to new cosmetic compositions which are pressurized as aerosols and which are capable of spontaneously forming a foam on contact with a surface, in particular human keratinous material such as hair.

Various presentation forms are used for dispensing cosmetic products onto keratinous material to be treated. In particular, the products packaged as aerosols and which instantaneously produce foam on departure from the distribution head of the container holding them are widely used in the field of hair products, such as styling or care products.

The method of use of these pressurized aerosol products consists in withdrawing foam into the hand on its departure from the container, and in applying this foam to the hair by spreading it with the hands. Any additional handling of the container, for example to add foam to the hand, results in a dirty mark on the container and/or a risk of dropping it. It is therefore necessary for the hands to be washed after use, especially, if a hair dryer has to be used to dry the hair and/or to carry out blow drying.

It has now been discovered that a solution to this problem consists in no longer placing the foam directly on the hand but rather, in spraying a specific composition, which departs from the container in the preferred form of a cloud of liquid particles and is then spontaneously converted to foam, but with a certain delay time reckoning from the departure from the container, on contact with the application surface.

The present invention therefore is directed to a cosmetic composition comprising a pressurized aerosol composition spontaneously forming a foam on contact with an application surface, in particular keratinous material such as hair, the aerosol composition comprising:

(i) an aqueous vehicle containing at least one foaming anionic polymer and/or at least one foaming cationic polymer; and (ii) a mixture of propellants containing dimethyl ether and at least one other propellant selected from volatile alkanes and volatile haloalkanes.

The present invention is also directed to an aerosol container which comprises the above defined composition.

The present invention also contemplates a process for treating keratinous material, in particular hair, which comprises applying at least one composition as defined above to the keratinous material.

A further embodiment of the present invention includes the use of a composition as defined above for application before or after any hair treatment, such as shampooing, dyeing or bleaching, permanent waving or hair straightening; as a hair setting, blow drying, hair shaping or styling composition; or as a dyeing, bleaching, permanent waving or hair straightening composition.

A still further embodiment of the present invention includes a method of applying a cosmetic composition to a surface comprising the step of spraying particles of pressurized aerosol composition onto an application surface, in particular keratinous material such as hair, the composition spontaneously forming a foam on contact with the surface, and the aerosol composition comprising:

(i) an aqueous vehicle containing at least one foaming anionic polymer and/or at least one foaming cationic polymer; and (ii) a mixture of propellants including dimethyl ether and at least one other propellant selected from volatile alkanes and volatile haloalkanes.

BRIEF DESCRIPTION OF THE FIGURE

The FIGURE is a perspective view of a conventional aerosol can for use in dispensing the composition according to the present invention. In the FIGURE, the aerosol can 10 includes a distribution head 12 that when depressed emits the enclosed composition. Aerosol cans of this type are well known in the art.

According to the invention, the foam is not formed on departure from the container but only on contact with the application surface. This is known as a delayed effect. It is therefore easy to confine the foam to the desired application surfaces. Moreover, spraying a cloud of particles makes possible homogeneous distribution. In the absence of dimethyl ether, the delayed effect mentioned above cannot be obtained.

According to the invention, the compositions can further contain ingredients commonly used in cosmetic compositions, but it is necessary that these ingredients do not prevent foam formation. The formed foam is preferably short-lived, that is to say, that the foam quickly disappears after its formation, without it being necessary to work it with the hands. Short-lived, as defined herein, means less than one minute, preferably less than 30 seconds and more preferably less than 15 seconds.

A foaming polymer is understood herein to mean a polymer which in 0.5% (by weight) aqueous solution gives, according to temperature modified (20° C.) Ross Miles Test (AFNOR T 73 404), a foam height of 1 cm and gives, after pressurization, a foam amount such that its volumic mass is smaller than 0.4, and preferably smaller than 0.25 g/cm3. These tests are described in French Patent No. 2,505,348, which is incorporated in the present application by reference. According to the invention, it is possible to use any anionic or cationic polymer known in the art which satisfies these tests.

Anionic polymers which may be used in the present invention are polymers which contain groups derived from carboxylic, sulphonic or phosphonic acid and which have a molecular weight ranging from approximately 500 to 5,000,000. The carboxyl groups are introduced by unsaturated mono- or dicarboxylic acid monomers such as those corresponding to the formula (I):

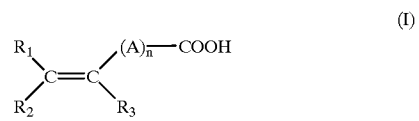

in which:

n is an integer ranging from 0 to 10; A represents a methylene group, which may be connected to the carbon atom of the unsaturated group or to the neighbouring methylene group when n is greater than 1 via a heteroatom such as oxygen or sulphur; $R_1$ represents a hydrogen atom, a phenyl or benzyl group; $R_2$ represents a hydrogen atom or a lower alkyl or carboxyl group; and $R_3$ represents a hydrogen atom, a lower alkyl group or a —$CH_2$—COOH, phenyl or benzyl group. In the above-mentioned formula, a lower alkyl radical preferably represents a group having from 1 to 6 carbon atoms and preferably, from 1 to 4 carbon atoms, and more preferably, methyl or ethyl. One skilled in the art readily understands that an alkyl radical, when there are at least 3 carbon atoms therein, may be linear or branched.

The preferred anionic polymers containing carboxyl groups according to the invention are:

(A) homo- or copolymers of acrylic or methacrylic acid or their salts, and preferably the products sold under the names Versicol E or K by the company Allied Colloid or Ultrahold by the company BASF; copolymers of acrylic acid and acrylamide, sold in the form of their sodium salt under the names Reten 421, 423 or 425 by the company Hercules; or sodium salts of polyhydroxycarboxylic acids;

(B) copolymers of acrylic or methacrylic acid with a monoethylenic monomer such as ethylene, styrene, vinyl esters or esters of acrylic or methacrylic acid which may be grafted onto a polyalkylene glycol such as polyethylene glycol and which may be crosslinked. Such polymers are described in particular in French Patent No. 1,222,944 and German Patent Application No. 2,330,956, the disclosures of which are incorporated herein by reference. Copolymers of this type containing in their chain an optionally N-alkylated and/or hydroxyalkylated acrylamide unit are described particularly in Luxembourg Patent Applications 75370 and 75371 or proposed under the name Quadramer by the Company American Cyanamid. The copolymers of acrylic acid and alkyl(C1–C4)methacrylate and terpolymers of vinylpyrrolidone, acrylic acid and alkyl(C1–C20) methacrylate such as vinylpyrrolidone/acrylic acid/laurylmethacrylate terpolymer sold under the name ACRYLIDONE LM by the company ISP may also be mentioned;

(C) copolymers derived from crotonic acid, such as those containing in their chain vinyl acetate or propionate units and optionally other monomers such as allyl or methallyl esters, vinyl ether or vinyl ester of a linear or branched saturated carboxylic acid with a long hydrocarbon chain, such as those containing at least 5 carbon atoms; it being possible for these polymers to be optionally grafted and/or crosslinked; or alternatively a vinyl, allyl or methallyl ester of an α or β-cyclic carboxylic acid. Such polymers are described, inter alia, in French Patents 1,222,944, 1,580,545, 2,265,782, 2,265,781, 1,564,110 and 2,439,798, the disclosures of which are incorporated herein by reference. Commercial products coming within this class are the resins 28-29-30, 26-13-14 and 28-13-10 sold by the company National Starch;

(D) polymers, including copolymers and homopolymers, derived from maleic, fumaric and itaconic acids or anhydrides with vinyl esters, vinyl ethers, vinyl halides, phenylvinyl derivatives or acrylic acid and its esters, which polymers can be esterified. Such polymers are described in particular in U.S. Pat. Nos. 2,047,398, 2,723,248 and 2,102,133, and in Great Britain Patent No. 839,805, the disclosures of which are incorporated herein by reference, and particularly sold under the names Gantrez AN or ES by the company ISP. Polymers which also come within this class are copolymers of maleic, citraconic and itaconic anhydrides and of an allyl or methallyl ester optionally containing an acrylamide or methacrylamide group or an α-olefin, acrylic or methacrylic esters, acrylic or methacrylic acid or vinylpyrrolidone in their chain, the anhydride functional groups being monoesterified or monoamidified, as described in French Patents 2,350,384 and 2,357,241; and (E) polyacrylamides containing carboxylate groups.

The polymers comprising sulpho groups may be polymers containing vinylsulphonic, styrenesulphonic, lignosulphonic or acrylamido-alkylsulphonic units. These polymers may preferably be chosen from: the salts of polyvinylsulphonic acid having a molecular weight ranging from approximately 1000 to 100,000, as well as the copolymers with an unsaturated comonomer such as acrylic or methacrylic acid and its esters as well as acrylamide, vinyl ethers and vinyl pyrrolidone; the salts of polystyrenesulphonic acid; the sodium salts having a molecular weight ranging from approximately 500,000 to approximately 100,000 sold respectively under the names Flexan 500 and Flexan 130 by National Starch (these compounds are described in French Patent No. 2,198,719, the disclosure of which is incorporated herein by reference); the alkali metal and alkaline-earth metal salts of the sulphonic acids derived from lignin, and more particularly calcium or sodium lignosulphonates such as the product sold under the name Marasperse C-21 by American Can Co. and the $C_{10}$–$C_{14}$ derivatives sold by Avébène; the salts of poly-acrylamidesulphonic acids, such as those mentioned in U.S. Pat. No. 4,128,631, the disclosure of which is incorporated herein by reference, and more particularly polyacrylamidoethylpropane-sulphonic acid sold under the name Cosmedia Polymer HSP 1180 by Henkel.

According to the invention, the anionic polymers are more preferably chosen from the copolymers of acrylic acid such as the acrylic acid/ethyl acrylate/N-tert-butylacrylamide terpolymer sold under the name Ultrahold Strong by the company BASF; the copolymers derived from crotonic acid such as the vinyl acetate/vinyl tert-butylbenzoate/crotonic acid terpolymers and the crotonic acid/vinyl acetate/vinyl neododecanoate terpolymers sold under the name Resin 28-29-30 by the company National Starch or the polymers derived from maleic, fumaric and itaconic acids or anhydrides with vinyl esters, vinyl ethers, vinyl halides, phenylvinyl derivatives or acrylic acid and its esters such as the methyl vinyl ether/monoesterified maleic anhydride copolymer sold under the name Gantrez ES 425 by the company ISP.

Cationic polymers, which may be used in the present invention, are described for example in French Patent No. 2,505,348, which is incorporated in the present application by reference.

The cationic polymers with a foaming ability may preferably be chosen from the following compounds: crosslinked polyamine/polyglycol copolymers such as the products sold under the names Polyquart by the company Henkel; cationic cellulose ethers corresponding to the formula (II):

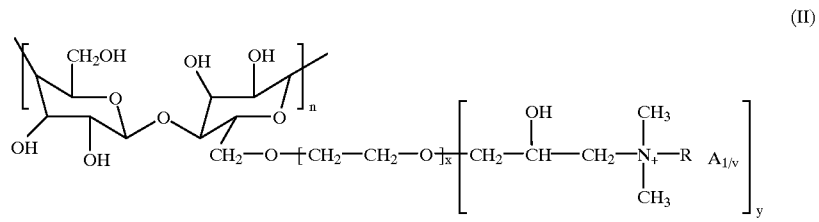

in which:

R is an alkyl radical having at least 8 carbon atoms, preferably 10 to 24 carbon atoms and more preferably 10 to 18 carbon atoms; $A^-$ is an anion or a mixture of anions; v is equal to the valency of A; n is an integer ranging from 50 to 20,000, preferably 100 to 6000 and more preferably 250 to 4000; x is an integer ranging from 0 to 6; and y is an integer ranging from 0 to 3, preferably from 0 to 2; with the proviso that the degree of cationic substitution, CS, is greater than 0. One skilled in the art would understand that an alkyl group having 3 or more carbon atoms may be linear or branched. These compounds, and their preparation, are described in European Patent No. EP-A-189,935, the disclosure of which is incorporated herein by reference. The degree of cationic substitution (or of quaternization), CS, is defined as the molar mean of the quaternary nitrogen atoms per cellulose repeat unit. This degree is greater than 0, preferably less than 1, and more preferably ranges from 0.01 to 0.6. A particularly preferred cationic cellulose ether of formula (II) is sold under the name Quatrisoft LM 200 by the company Amerchol.

According to a preferred embodiment of the invention, the composition contains a foaming anionic polymer and more preferably a foaming anionic polymer in combination with a foaming or non-foaming cationic polymer. A more particularly preferred anionic polymer/cationic polymer combination according to the invention is a combination comprising a methyl vinyl ether/monoesterified maleic anhydride copolymer and a hydroxyethyl cellulose/diallyldimethylammonium chloride copolymer. The polymer(s) may be present in concentrations ranging from 0.1% to 15% by weight, and preferably in concentrations ranging from 0.5% to 10% by weight, with respect to the total weight of the composition.

According to the invention, propellent is understood to mean any fluid which has a boiling point of less than 40.6° C.

The volatile alkane is preferably chosen from isobutane, propane, butane, pentane and isopentane. The volatile haloalkane is preferably chosen from bromoalkanes, iodoalkanes and fluoroalkanes, and more preferably chosen from difluoroethanes, tetrafluoroethanes, octafluorocyclobutane and mixtures thereof. According to a particularly preferred embodiment of the present invention, the mixture of propellants consists of dimethyl ether and isobutane.

The dimethyl ether/other propellant(s) mixture is preferably present in amounts ranging from 5% to 55% by weight with respect to the total weight of the composition and more preferably in amounts ranging from 15% to 35% by weight. Dimethyl ether is preferably present in amounts ranging from 4% to 35% by weight with respect to the total weight of the composition. The other propellant(s) is/are preferably present in amounts ranging from 1% to 20% by weight with respect to the total weight of the composition and more preferably from 2% to 15% by weight. The ratio (by weight) of dimethylether/other propellant(s) can range from 95/5 to 50/50 and preferably ranges from 90/10 to 55/45.

The aqueous liquid vehicle used for preparing the compositions in accordance with the invention must allow a foam to be formed on contact with the application surface, in particular keratinous material such as hair, preferably a short-lived foam. According to the invention, the vehicle comprises, for example, water and can optionally contain cosmetically acceptable solvents preferably chosen from ethanol and isopropanol. The amount of solvent is such that it does not disrupt the foaming nature of the composition. The amount of solvent is preferably less than 20% (by weight) with respect to the total weight of the composition. According to the invention, water is preferably present in amounts ranging from 20% to 90% and more preferably in amounts ranging from 40% to 80% with respect to the total weight of the composition.

The compositions according to the invention can additionally contain ingredients commonly used in cosmetic compositions, for example, those ingredients used for hair dyeing, bleaching, permanent waving, straightening, setting, blow drying, shaping, or styling, provided that such ingredients do not disturb the self-foaming nature of the compositions according to the invention. Typical ingredients include, for example, peptizing agents, surface-active agents, treating agents, basifying or acidifying agents, preserving agents, fragrances, silicones (volatile or non-volatile, functionalized or non-functionalized), anticorrosion agents, dyes, sunscreening agents, proteins, vitamins, other polymers, vegetable, animal, inorganic or synthetic oils and any other additive used in this type of composition. One of the advantages of the compositions according to the invention is that they can be free of any surface-active agent.

The composition of the invention can be used more particularly as a hair composition whose application on dry or wet hair is optionally followed by rinsing with water. The invention also relates to the use of this composition as a composition to be applied before or after any hair treatment such as shampooing, dyeing or bleaching, permanent waving or hair straightening. The present invention more particularly relates to the use of this composition as a hair setting, blowing drying, hair shaping or styling composition. The invention also relates to the use of this composition as a dyeing, bleaching, permanent waving or hair straightening composition for hair. A further subject of the invention is a process for treating keratinous material, in particular hair, which comprises applying a composition as defined above to the keratinous material.

In the following examples, given by way of illustration and without implied limitation, concrete compositions in accordance with the invention are given.

EXAMPLE 1

A composition having the following characteristics was prepared:

| | |
|---|---|
| Methyl vinyl ether/monobutyl maleate copolymer as a 50% solution of active material in ethanol, sold under the name Gantrez ES 425 by the company ISP | 4 g AM |
| 2-Amino-2-methylpropanol q.s. | pH 8.5 |
| Fragrance, preserving agent q.s. | |
| Water q.s. for | 100 g |

This composition can be packaged according to the following pressurization plan:

| | |
|---|---|
| Composition as described above | 70% |
| Isobutane | 10% |
| Dimethyl ether | 20% |

The pressurized composition can be sprayed onto wet hair in the form of a cloud of liquid particles and a foam should then develop on the hair. This non-stick foam should rapidly disappear on the hair. The dried hair should be soft to the touch and have a good hold.

EXAMPLE 2

A composition having the following characteristics was prepared:

| | |
|---|---|
| Acrylic acid/ethyl acrylate/N-tert-butylacrylamide terpolymer sold under the name Ultrahold Strong by the company BASF | 2 g |
| 2-Amino-2-methylpropanol q.s. | pH 8 |
| Fragrance, preserving agent q.s. | |
| Water q.s. for | 100 g |

This composition can be packaged according to the following pressurization plan:

| | |
|---|---|
| Composition as described above | 75% |
| Isobutane | 8% |
| Dimethyl ether | 17% |

When sprayed onto wet hair, this composition should give the same results as in Example 1.

EXAMPLE 3

A composition having the following characteristics was prepared:

| | |
|---|---|
| Methyl vinyl ether/monobutyl maleate copolymer as a 50% solution of active material in ethanol, sold under the name Gantrez ES 425 by the company ISP | 3.5 g AM |
| Hydroxyethyl cellulose/diallyldimethyl-ammonium chloride copolymer sold under the name Celquat L 200 by the company National Starch | 2 g |
| 2-Amino-2-methylpropanol q.s. | pH 8 |
| Ethanol | 10 g |
| Fragrance, preserving agent q.s. | |
| Water q.s. for | 100 g |

This composition can be packaged according to the following pressurization plan:

| | |
|---|---|
| Composition as described above | 70% |
| n-Butane | 10% |
| Dimethyl ether | 20% |

When sprayed onto wet hair, this composition should give the same results as in Example 1.

EXAMPLE 4

A composition having the following characteristics was prepared:

| | |
|---|---|
| Quaternized hydroxyethyl cellulose (Polyquaternium-24 according to the CTFA nomenclature, 4th ed., 1992) sold under the name Quatrisoft LM 200 by the company Amerchol | 1 g |
| Fragrance, preserving agent q.s. | |
| Water q.s. for | 100 g |

This composition can be packaged according to the following pressurization plan:

| | |
|---|---|
| Composition as described above | 75% |
| n-Butane | 10% |
| Dimethyl ether | 15% |

When sprayed onto wet hair, this composition should give the same results as in Example 1.

What is claimed is:

1. A cosmetic composition comprising a pressurized aerosol composition, said aerosol composition comprising:
   (i) an aqueous vehicle containing at least one foaming anionic polymer and/or at least one foaming cationic polymer; and
   (ii) a mixture of propellants containing dimethyl ether and at least one other propellant selected from volatile alkanes and volatile haloalkanes, wherein the ratio of dimethyl ether/other propellants ranges from 95/5 to 50/50; and
   wherein said aerosol composition spontaneously forms a foam on contact with an application surface.

2. A composition according to claim 1, wherein said at least one foaming anionic polymer may be selected from:
   (A) polymers containing carboxyl units derived from unsaturated mono- or dicarboxylic acid monomers of the formula:

(I)

in which:
   n is an integer ranging from 0 to 10; A represents a methylene group, which may be connected to the carbon atom of the unsaturated group or to the neighbouring methylene group when n is greater than 1 via a heteroatom; $R_1$ represents a hydrogen atom, a phenyl or a benzyl group; $R_2$ represents a hydrogen atom or a lower alkyl or carboxyl group; and $R_3$ represents a hydrogen atom, a lower alkyl group or a —$CH_2$—COOH, phenyl or benzyl group; and
   (B) polymers containing units derived from a sulphonic acid.

3. A composition according to claim 2, wherein said heteroatom is oxygen or sulphur.

4. A composition according to claim 2, wherein said units derived from sulphonic acid are selected from vinyl sulphonic, strenesulphonic, lignosulphonic, and acrylamidoalkylsulphonic units.

5. A composition according to claim 1, wherein said at least one foaming anionic polymer may be selected from:
   (A) homo- or copolymers of acrylic or methacrylic acid or their salts; copolymers of acrylic acid and acrylamide and their salts; and sodium salts of polyhydroxcarboxylic acids;
   (B) copolymers of acrylic or methacrylic acid with a monoethylenic monomer which copolymers may be grafted onto a polyalkylene glycol and/or which copolymers may be crosslinked; wherein said copolymers of acrylic or methacrylic acid with a monoethylenic monomer may additionally contain in their chain an N-alkylated and/or hydroxyalkylated acrylamide unit; copolymers of acrylic acid and alkyl(C1–C4)

methacrylate; and terpolymers of vinlypyrrolidone, acrylic acid, and alkyl(C1–C20)methacrylate;

(C) copolymers derived from crotonic acid, which copolymers may be grafted and/or crosslinked;

(D) polymers derived from maleic, fumaric and itaconic acids or anhydrides with vinyl esters, vinyl ethers, vinyl halides, phenylvinyl derivatives or acrylic acid and its esters; copolymers of maleic, citraconic and itaconic anhydrides and of an allyl or methallyl ester which may contain an acrylamide or methacrylamide group or an α-olefin, acrylic or methacrylic ester, acrylic or methacrylic acid or vinylpyrrolidone in their chain, the anhydride functional groups being monoesterified or monoamidified; and (E) polyacrylamides containing carboxylate groups.

6. A composition according to claim 5, wherein said monoethylenic monomer in (B) may be selected from ethylene, styrene, vinyl esters and esters of acrylic or methacrylic acid.

7. A composition according to claim 5, wherein said polyalkylene glycol in (B) is polyethylene glycol.

8. A composition according to claim 5, wherein said copolymer derived from crotonic acid in (C) may be selected from those which contain vinyl acetate or propionate units in their chain.

9. A composition according to claim 8, wherein said copolymer derived from crotonic acid in (C) also contains other monomers which may be selected from allyl or methallyl esters, vinyl esters or a vinyl ester of a linear or branched carboxylic acid with a long hydrocarbon chain.

10. A composition according to claim 9, wherein said long hydrocarbon chain contains at least 5 carbon atoms.

11. A composition according to claim 1, wherein said at least one foaming anionic polymer may be selected from:

(A) copolymers of acrylic acid;

(B) copolymers derived from crotonic acid; and (C) polymers derived from maleic, fumaric and itaconic acids or anhydrides with vinyl esters, vinyl ethers, vinyl halides, phenylvinyl derivatives or acrylic acid and its esters.

12. A composition according to claim 11, wherein said copolymer derived from crotonic acid may be selected from vinyl acetate/vinyl tert-butylbenzoate/crotonic acid terpolymers and crotonic acid/vinyl acetate/vinyl neododecanoate terpolymers.

13. A composition according to claim 11, wherein said copolymer of acrylic acid is acrylic acid/ethyl acrylate/N-tert-butylacrylamide terpolymer.

14. A composition according to claim 11, wherein said polymers derived from maleic, fumaric, and itaconic acids or anhydrides may be selected from methyl vinyl ether/monoesterified maleic anhydride copolymers.

15. A composition according to claim 1, wherein said at least one foaming cationic polymer is selected from:

(A) crosslinked polyamine/polyglycol copolymers;

(B) cationic cellulose ethers corresponding to formula (II):

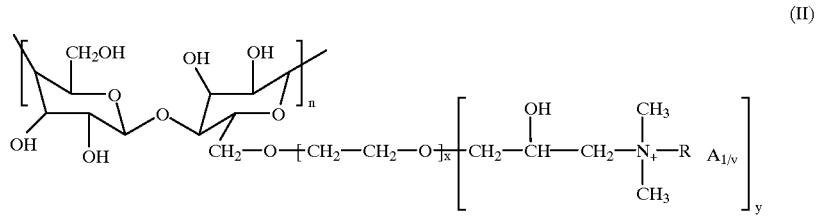

in which:

R is an alkyl radical having at least 8 carbon atoms; A$^-$ is an anion or a mixture of anions; v is equal to the valency of A; n is an integer ranging from 50 to 20,000; x is an integer ranging from 0 to 6; and y is an integer ranging from 0 to 3; with the proviso that the degree of cationic substitution, CS, is greater than 0.

16. A composition according to claim 15, wherein R is an alkyl radical having from 10 to 24 carbon atoms; n is an integer ranging from 100 to 6000; and y is an integer ranging from 0 to 2.

17. A composition according to claim 16, wherein R is an alkyl radical having from 10 to 18 carbon atoms; and n is an integer ranging from 250 to 4000.

18. A composition according to claim 1, wherein said at least one polymer is present in a concentration ranging from 0.1% to 15% by weight with respect to the total weight of the composition.

19. A composition according to claim 18, wherein said at least one polymer is present in a concentration ranging from 0.5% to 10% by weight with respect to the total weight of the composition.

20. A composition according to claim 1, wherein said volatile alkane is selected from isobutane, propane, butane, pentane, isopentane, and mixtures thereof.

21. A composition according to claim 1, wherein said volatile haloalkane is selected from bromoalkanes, iodoalkanes, fluoroalkanes, and mixtures thereof.

22. A composition according to claim 21, wherein said volatile haloalkane is selected from difluoroethanes, tetrafluoroethanes, octafluorocyclobutane and mixtures thereof.

23. A composition according to claim 1, wherein said mixture of propellants comprises dimethyl ether and isobutane.

24. A composition according to claim 1, wherein said mixture of propellants is present in an amount ranging from 5% to 55% by weight with respect to the total weight of the composition.

25. A composition according to claim 24, wherein said mixture of propellants is present in an amount ranging from 15% to 35% by weight with respect to the total weight of the composition.

26. A composition according to claim 1, wherein said dimethyl ether is present in an amount ranging from 4% to 35% by weight with respect to the total weight of the composition.

27. A composition according to claim 1, wherein said at least one other propellant is present in an amount ranging from 1% to 20% by weight with respect to the total weight of the composition.

28. A composition according to claim 1, wherein the ratio by weight of dimethyl ether/other propellants ranges from 90/10 to 55/45.

29. A composition according to claim 1, which comprises a foaming anionic polymer and a foaming or non-foaming cationic polymer.

30. A composition according to claim 29, which comprises a methyl vinyl ether/monoesterified maleic anhydride copolymer and a hydroxyethyl cellulose/diallyldimethylammonium chloride copolymer.

31. An aerosol container, which comprises a composition according to claim 1.

32. A process for treating keratinous material, which comprises applying at least one composition as claimed in claim 1 to said keratinous material.

33. A process according to claim 32, wherein said keratinous material is hair.

34. A method of using the composition according to claim 1, which comprises applying said composition to hair before or after said hair has received a treatment or applying said composition to hair as a setting, blow drying, shaping, styling, dyeing, bleaching, permanent waving or straightening composition for hair.

35. The method of claim 34, wherein said treatment includes dyeing, bleaching, permanent waving, straightening, or blow drying.

36. A method of using the composition according to claim 1, which comprises applying said composition to hair together with an effective amount of an ingredient to dye, bleach, permanent wave, straighten, set, blow dry, shape, or style said hair.

37. A composition according to claim 1, wherein said application surface is human keratinous material.

38. A composition according to claim 37, wherein said human keratinous material is hair.

39. A method of applying a cosmetic composition to a surface, comprising the step of spraying particles of pressurized aerosol composition onto an application surface, said composition spontaneously forming a foam on contact with said surface, and said aerosol comprising:
   (l) an aqueous vehicle containing at least one foaming anionic polymer and/or at least one foaming cationic polymer; and
   (ii) a mixture of propellants including dimethyl ether and at least one other propellant selected from volatile alkanes and volatile haloalkanes, wherein the ratio of dimethyl ether/other propellants ranges from 95/5 to 50/50.

40. A method according to claim 39, wherein said particles are sprayed in the form of a cloud and wherein said surface is hair.

41. A method according to claim 40, wherein said foam is short-lived.

42. A method according to claim 41, wherein said foam disappears in less than 30 seconds.

43. A method according to claim 42, wherein said foam disappears in less than 15 seconds.

44. A method according to claim 39, wherein said spraying step provides a homogeneous distribution of said particles on said surface.

45. A composition according to claim 1, wherein said aqueous vehicle further comprises water in an amount ranging from 20% to 90% with respect to the total weight of the composition.

46. A composition according to claim 45, wherein said water is present in an amount ranging from 40% to 80% with respect to the total weight of the composition.

47. A composition according to claim 1, wherein said aqueous vehicle further comprises at least one cosmetically acceptable solvent selected from ethanol and isopropanol, wherein said at least one solvent is present in an amount less than 20% with respect to the total weight of the composition.

* * * * *

UNITED STATES PATENT AND TRADEMARK OFFICE
CERTIFICATE OF CORRECTION

PATENT NO.: 6,113,923

DATED: September 5, 2000

INVENTORS: Le Bourhis

It is certified that errors appear in the above-identified patent and that said Letters Patent is hereby corrected as shown below:

Claim 1, col. 8, line 18, begin a new unindented line with "wherein the ratio of".

Claim 39, col. 12, line 9, begin a new unindented line with "wherein the ratio of".

Signed and Sealed this

Twenty-fourth Day of April, 2001

Attest:

NICHOLAS P. GODICI

Attesting Officer

Acting Director of the United States Patent and Trademark Office